(12) United States Patent
Markley et al.

US006274707B1

(10) Patent No.: US 6,274,707 B1
(45) Date of Patent: Aug. 14, 2001

(54) PROTEIN SWEETENER

(75) Inventors: John L. Markley; Fariba M. Assadi-Porter, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/291,349

(22) Filed: Apr. 14, 1999

(51) Int. Cl.[7] ....................................................... C07K 1/00
(52) U.S. Cl. .......................... 530/350; 530/350; 530/324; 530/379; 435/6; 435/69.1; 435/172.3; 435/320.1; 435/410; 536/23.1; 536/23.6; 426/548; 800/205
(58) Field of Search ................................ 435/69.1, 172.3, 435/320.1, 410, 6; 530/350, 324, 379; 536/23.6, 23.1; 426/548; 800/205

(56) References Cited

U.S. PATENT DOCUMENTS 5,221,624   6/1993   Blair et al. ........................ 435/252.33
5,346,998   9/1994   Hellekant et al. ................... 536/23.6
5,527,555   6/1996   Hellekant et al. ..................... 426/548

FOREIGN PATENT DOCUMENTS

94/19467        9/1994   (WO) .
WO 95/31547  * 11/1995   (WO) .

OTHER PUBLICATIONS

Alignments, Ming et al. FEBS Letters, vol. 355, pp. 106–108, 1994.*
Ming et al., FEBS Letters, vol. 355, pp. 106–108, 1994.*
Alignments, Hellenkant et al., 1995.*

* cited by examiner

*Primary Examiner*—Karen Cochrane Carlson
*Assistant Examiner*—Hope A. Robinson
(74) *Attorney, Agent, or Firm*—Quarles & Brady LLP

(57) ABSTRACT

Disclosed herein are sweet proteins that are variants of Brazzein, and nucleotide sequences capable of expressing them. Through a replacement of an amino acid in the naturally occurring Brazzein sequence with Arg or Ala (or the addition of Arg or Ala), the taste profile and sweetness strength can be changed.

12 Claims, 1 Drawing Sheet

US 6,274,707 B1

PROTEIN SWEETENER

STATEMENT REGARDING FEDERALLY SPONSORED RESEARCH

This invention was made with United States government support awarded by the following agency: NIH GM35976 The United States Government has certain rights in this invention

CROSS REFERENCE TO RELATED APPLICATIONS

Not applicable.

BACKGROUND OF THE INVENTION

The present invention relates to sweet proteins. Brazzein protein that has been modified to improve its taste profile and to permit sweetness perception at significantly lower concentrations is disclosed.

The most widely used natural sweetener, sugar (sucrose), has significant problems associated with its use (especially causing weight gain by users). Many other sweeteners either have undesirable side effects or are deficient in certain respects. For example, aspartame loses its sweetness when exposed to elevated temperatures for long periods. This renders aspartame unsuitable for use in most baking applications. Moreover, most existing artificial sweeteners have temporal sweetness profiles which do not adequately match that of sugar. For example, their sweetness may die out sooner or leave an undesirable after taste, and/or may be perceived sooner than sugar. It may therefore be desirable to mix an existing artificial sweetener with one or more other sweeteners having different temporal profiles (so as to create a mixed sweetener that more closely matches the overall temporal sweetness profile of sugar).

Only relatively few sweet proteins (as distinguished from sweet carbohydrates) have been found in nature. One protein that appears to be particularly promising is Brazzein (SEQ ID NO: 1). See also U.S. Pat. Nos. 5,346,998 and 5,527,555, PCT publication WO 94/19467, and J. Caldwell et al., Solution Structure Of The Thermostable Sweet-tasting Protein Brazzein, 5 Nature Structural Biology 427–431 (1998). This protein is particularly desirable because it is stable when subjected to the level of heat typically present during baking of foods. The disclosure of these publications and of all other publications referred to herein are incorporated by reference as if fully set forth herein.

While naturally occurring Brazzein has certain desirable characteristics, there are some concerns regarding its temporal profile and the amount of the sweetener needed for threshold perception. Moreover, recombinant expression systems for Brazzein have to date been relatively inefficient. Prior research had not been able to identify any consensus sequence or structure in Brazzein responsible for sweetness or the sweetness profile. Thus, efforts to date to improve Brazzein's sweetness characteristics were not successful.

As such, it can be seen that the need exists for an improved protein sweetener.

BRIEF SUMMARY OF THE INVENTION

In one aspect the invention provides a peptide comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14.

In another aspect, the invention provides a peptide having the SEQ ID NO: 1 amino acid sequence, albeit with one additional Ala either inserted therein, or inserted therein in replacement for an amino acid other than Ala in SEQ ID NO: 1, or positioned at a terminus of SEQ ID NO: 1.

In yet another aspect, the invention provides a peptide having the SEQ ID NO: 1 amino acid sequence, albeit with one additional Arg either inserted therein, or inserted therein in replacement for an amino acid other than Arg in SEQ ID NO: 1, or positioned at a terminus of SEQ ID NO: 1.

Other forms of the invention include providing nucleotide sequences for expressing such peptides. For example, a SEQ ID NOS: 15 and 17 are sequences capable of expressing SEQ ID NO: 3 and SEQ ID NO: 9 respectively.

Surprisingly, it has been learned that the replacement of a single amino acid in SEQ ID NO: 1 with either Ala or Arg, or the addition of either, can create peptides with desirable sweetness characteristics. For example, the addition of a single Ala at the beginning of the SEQ ID NO: 1 sequence to create SEQ ID NO: 3, or the replacement of one His with Ala, leads to a substantially lower detectable threshold of sweetness.

The sweet proteins of the present invention will be useful to sweeten consumable foods and beverages. For example, a small amount of the peptide can be mixed in a carrier such as lactose and poured into a beverage such as ice tea in order to sweeten it.

Further, production of genes coding for these peptides and their insertion into production vectors will allow large quantities to be created at low cost. Further, the genes can be inserted directly into a plant genome (and even possibly an animal genome) so that the fruit, vegetables, and/or edible meats, milk or the like may be sweeter.

The objects of the present invention therefore include providing:

(a) improved protein sweeteners that are stable when exposed for long periods of time to elevated temperatures;

(b) improved protein sweeteners which can be detected by humans at concentrations lower than concentrations usually required for Brazzein to be detected; and (c) genes coding for such protein sweeteners. These and still other objects and advantages of the present invention will be apparent from the description which follows. The following description is merely of the preferred embodiments. Thus, the claims should be looked to in order to understand the full scope of the invention.

DETAILED DESCRIPTION

Figure 1:
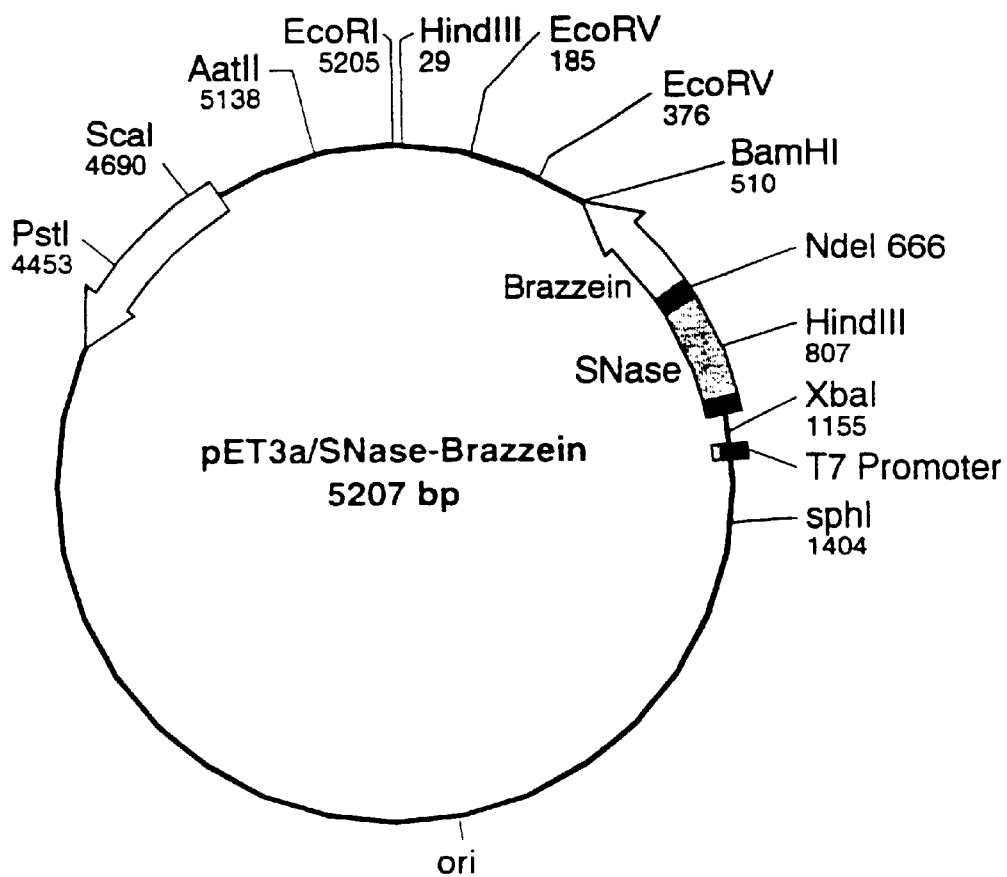
FIG. 1 is a schematic depiction of an expression vector useful in producing the peptides of the present invention.

SEQ ID NO: 1 (Brazzein) is available in natures and in any event can be produced in accordance with U.S. Pat. No. 5,527,555. We developed an improved expression vector for expressing Brazzein, and then used site directed mutagenesis (using the same parental vector) to efficiently express the peptides of the present invention.

Restriction enzymes and T4 DNA ligase were purchased from Promega (Madison, Wis.). *E. coli* strains, HMS174 (DE3, recA) and BL21 (DE3)/pLysS were purchased from Novagen (Madison, Wis.). Protein expression vectors pET-3a, pET-9a, pET-11a, and pET-16b were purchased from Novagen (Madison, Wis.). All purchased plasmids were stored in a non-expression host strain HMS174 and expressed in BL21 (DE3)/pLysS.

Nde I and Bam HI sites were designed into the 5' and 3' ends, respectively, to permit cloning into any of the pET system plasmids (a variety of plasmids characterized by a T7 expression system with an optional fusion to a polyhistidine linker). In addition, a starting codon (Met) was introduced just before the first codon of the synthetic gene, since the amino acid sequence of natural Brazzein lacked an N-terminal methionine.

The Brazzein gene was synthesized by ligating eight oligonucleotides per strand. The Nde I/Bam HI fragment of the resulting DNA, which contained the entire sequence des-Glp-Brazzein, was isolated and cloned into the T7 expression vector, pET-16b. The sequence of the final, ligated expression vector was confirmed by automated DNA sequencing. Mismatches due to errors during synthesis of original oligos were corrected by site-directed mutagenesis using PCR.

The synthetic Brazzein gene was cut with restriction enzymes and cloned into T7 expression vectors pET-3a, pET-9a, and pET-11a, which contain Nde I and Bam HI sites. The fusion construct was made with a modification of the original nuclease-ovomucoid fusion gene. A. Hinck et al., 6 Prot. Engin. 221–227 (1993).

The four Met codons in the nuclease gene (Snase) were replaced with Ala codons by quick-change site-directed mutagenesis (kit from Stratagene, La Jolla, Calif.). The DNA fragment coding for Brazzein (or the SNase-Brazzein fusion) was excised and cloned between Nde I and Bam HI sites at the C-terminus of the modified Snase gene in the pET-3a expression system. The resulting plasmid, named pET-3a/SNase-SW (see FIG. 1), was transformed into the $E.$ $coli$ strain BL21 (DE3)/pLysS for protein expression. The use of pLysS in this strain permits high-level expression of the nuclease-Brazzein fusion protein without the deleterious effect of nuclease.

A single colony of $E.$ $coli$ strain BL21 (DE3)/pLysS, containing the plasmid pET-3a/SNase-SW was selected and grown overnight at 37° C. in 5mL of Luria Broth medium with 100 μg ampicillin/mL and 34 μg of chloramphenicol/mL. The starting culture was used to inoculate 1L of LB medium with chloramphenicol (34 μg/mL)/ampicillin (100 μg/mL) at 37° C. until an $A_{600nm}$ of 0.8–1.0 was attained.

Cells were induced for 3 hours by the addition of isopropyl-β-D-galactopyranoside (IPTG) to a final concentration of 0.1 mM. Cells were harvested and rapidly frozen in liquid nitrogen and stored at −70° C. After freeze/thawing once, 4–5 g of cells were resuspended in 50 mL lysis buffer (50 mM Tris-HCl, pH=8.0, containing 2 mM EDTA and 10 mM PMSF). The lysed cells were treated with 10 mM $CaCl_2$ for a period of 15 minutes and subject to French pressing three times. The fully broken cells were centrifuged for 15 minutes at 12,000 g. The supernatant and the pellet were analyzed on 16% Tricine gels (Novex, San Diego, Calif.). More than 70% of the fusion protein was in insoluble form.

Where protein was present in inclusion bodies, the cell pellet after the French press steps was washed three times with lysis buffer. An extra wash step was carried out to ensure further purity of the inclusion body by adding nine volumes of lysis buffer containing 0.5% (v/v) Triton X-100 and 10 mM EDTA, waiting 5 minutes, and then centrifuging at 5,000×g for 10 minutes at 4° C.

The pellet was resuspended in 50 mL 8 M GdmCl containing 10 mM EDTA and 100 mM DTT and stirred for 2–3 hours at room temperature. The clear resuspension was dialyzed overnight at 4° C. against 4L deionized water ($dH_2O$) containing 3.5 mL acetic acid (pH–3.8–4.0) to ensure full protonation of the cysteine side chains. The precipitant was removed by centrifuging at 12,000×g.

The clear supernatant was dialyzed two more times against $dH_2O$ and acetic acid for a total period of 24 hours to completely remove the reducing agent. At this stage, more than 60–70% of the fusion protein was refolded, and the purity, as judged by gel electrophoresis, was greater that 80%. The typical yield of the fusion protein was 130–150 mg/L culture. The reduced sulfhydryl groups in the Brazzein domain were oxidized by rapidly diluting the dialyzate with 4–5 volumes of 200 mM Tris-acetic acid, pH 8.0, to a final concentration of 0.5–0.7 mg/mL (based on the SNase extinction coefficient, $\epsilon_{280,\ 1\%}=1.0$), and this solution was stirred at room temperature for 24 hours. Following the oxidization step, the solution was concentrated with an Amicon ultrafiltration apparatus to a final volume of 20–50 mL. When successfully folded and oxidized, the product was a clear solution. The concentrated fusion protein was dialyzed three times against 10L of $dH_2O$ to remove residual salt and lyophilized as white powder.

Lyophilized fusion protein (130–150 mg) was dissolved in 65–75 mL water to a final concentration of 2 mg/mL. The pH of the sample was adjusted to 1.5 by adding 1 M. Approximately 70–100 mg of CNBr was added to this solution, which was then stirred in the dark at room temperature for 24 hours. The cleaved product was lyophilized 4 times out of $dH_2O$ to ensure the complete removal of CNBr.

The white powder was dissolved in 30 mL 50 M Tris-HCl, pH 7.6, and applied to a CM-Sephadex column (2.5 cm×12 cm) pre-equilibrated with the same buffer. Pure Brazzein eluted in the first column volume. Nuclease and uncleaved fusion protein were eluted with 50 mM Tris-HCl, pH 7.6, containing 0.6 M NaCl. Brazzein-containing fractions were combined and desalted by dialysis against five changes of $dH_2O$ containing 0.1% acetic acid and lyophilized.

Brazzein variants were prepared by site directed mutagenesis using the same parental vector.

To test the sweetness profile and other sweetness characteristics of the peptides, we dissolved consistent amounts of these peptides in distilled water at room temperature and had a panel of consumers give their taste perceptions. The averaged results were as follows:

| SEQ ID NO: | Threshhold To Perceive Sweetness (μg/mL) | Sweetness Potency (Brazzein = 2,000) |
| --- | --- | --- |
| 1 | 25 | 4,000 |
| 2 | <<25 | >8,000 |
| 3 | <<25 | >8,000 |
| 4 | 200 | 500 |
| 5 | >600 | <167 |
| 6 | 400 | 250 |
| 7 | >600 | <167 |
| 8 | 50 | 2,000 |
| 9 | 100 | 1,000 |
| 10 | 25 | 4,000 |
| 11 | >600 | <167 |
| 12 | 200 | 500 |
| 13 | 25 | 4,000 |
| 14 | 100 | 1,000 |

These tests confirm that particular replacements (or insertions) using Ala or Arg vis a vis SEQ ID NO: 1 significantly varies (and in various cases greatly improves) sweetness profiles. Particularly with respect to SEQ ID NOS: 2 and 3, there was a marked reduction in the amount of peptide needed for threshold perception of sweetness compared to Brazzein, while retaining (and to some extent improving) other desirable sweetness characteristics.

Nearly one seventh of the amino acid composition of these peptides is lysine, an essential amino acid. Thus, not only are these sweeteners designed for desirable heat stability and sweetness temporal characteristics, they are a possible source of lysine.

Moreover, these peptides are so sweet that only a very small amount of them will be needed to sweeten coffee, tea, or the like. For such uses, they can be blended with a bulky filler (e.g. lactose) to give the user a feeling of perceived value.

Expression of cDNA

If one desires to produce, for example, the SEQ ID NO: 3 or 9 sweeteners, one could alternatively synthesize the SEQ ID NO: 15 and 17 DNA sequences respectively by combining standard cloning and automated synthesizer techniques (e.g. 380 B ABI DNA synthesizer). Each gene could then be cloned into an expression vector such as those described above, or pGEMEX®-1 (Promega) at the T7 gene 10 site (using conventional techniques). Such vectors could then be inserted into suitable hosts such as in the case of pGEMEX®-1 JM109 (DE3) (Promega), with expression in the usual manner.

For the other peptides, the modified portions of the gene sequence can be created by using gca, gcg, or gct for Ala, aac for Asn, and cgt for Arg.

The protein can then be harvested in the usual way (e.g. as part of a fusion protein). If desired, modifications can be made in conventional ways to reduce or eliminate undesired portions of the fusion proteins.

Alternatively, the proteins can be synthesized directly using a synthesizer.

It should also be possible to insert the cDNA into plant or animal genomes using known means to cause the gene to be expressed (thereby creating sweeter fruit, vegetables or meats).

Industrial Applicability

The invention provides sweet proteins that can be added to consumable items to impart a sweet flavor.

We claim:

1. A synthetically produced peptide having a different sweetness potency or sweetness temporal profile from naturally occurring Brazzein comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 12, SEQ ID NO: 13 and SEQ ID NO: 14.

2. The peptide of claim 1, wherein the amino acid sequence that is selected is SEQ ID NO: 2.

3. The peptide of claim 1, wherein the amino acid sequence that is selected is SEQ ID NO: 3.

4. The peptide of claim 1, wherein the amino acid sequence that is selected is SEQ ID NO: 4.

5. The peptide of claim 1, wherein the amino acid sequence that is selected is SEQ ID NO: 5.

6. The peptide of claim 1, wherein the amino acid sequence that is selected is SEQ ID NO: 6.

7. The peptide of claim 1, wherein the amino acid sequence that is selected is SEQ ID NO: 8.

8. The peptide of claim 1, wherein the amino acid sequence that is selected is SEQ ID NO: 9.

9. The peptide of claim 1, wherein the amino acid sequence that is selected is SEQ ID NO: 10.

10. The peptide of claim 1, wherein the amino acid sequence that is selected is SEQ ID NO: 12.

11. The peptide of claim 1, wherein the amino acid sequence that is selected is SEQ ID NO: 13.

12. The peptide of claim 1, wherein the amino acid sequence that is selected is SEQ ID NO: 14.

* * * * *

SEQUENCE LISTING

<160> NUMBER OF SEQ ID NOS: 18

<210> SEQ ID NO 1
<211> LENGTH: 53
<212> TYPE: PRT
<213> ORGANISM: Pentadiplandra brazzeana

<400> SEQUENCE: 1

Asp Lys Cys Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 2
<211> LENGTH: 53
<212> TYPE: PRT
<213> ORGANISM: Pentadiplandra brazzeana

<400> SEQUENCE: 2

Asp Lys Cys Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys Ala Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 3
<211> LENGTH: 54
<212> TYPE: PRT
<213> ORGANISM: Pentadiplandra brazzeana

```
<400> SEQUENCE: 3

Ala Asp Lys Cys Lys Lys Val Tyr Glu Asn Tyr Pro Val Ser Lys Cys
 1               5                  10                  15

Gln Leu Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
        50

<210> SEQ ID NO 4
<211> LENGTH: 53
<212> TYPE: PRT
<213> ORGANISM: Pentadiplandra brazzeana

<400> SEQUENCE: 4

Asp Lys Cys Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys His Ala Ala
            20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 5
<211> LENGTH: 53
<212> TYPE: PRT
<213> ORGANISM: Pentadiplandra brazzeana

<400> SEQUENCE: 5

Asp Lys Cys Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Ala Asn Leu Gln Cys Ile Cys
        35                  40                  45

Asp Tyr Cys Glu Tyr
        50

<210> SEQ ID NO 6
<211> LENGTH: 53
<212> TYPE: PRT
<213> ORGANISM: Pentadiplandra brazzeana

<400> SEQUENCE: 6

Asp Lys Ala Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 7
<211> LENGTH: 55
<212> TYPE: PRT
```

```
<213> ORGANISM: Pentadiplandra brazzeana

<400> SEQUENCE: 7

Asp Lys Cys Lys Lys Val Tyr Glu Asn Tyr Pro Val Ser Lys Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu Tyr Arg Arg
         50                  55

<210> SEQ ID NO 8
<211> LENGTH: 53
<212> TYPE: PRT
<213> ORGANISM: Pentadiplandra brazzeana

<400> SEQUENCE: 8

Asp Lys Cys Lys Lys Val Tyr Glu Asn Tyr Pro Val Ser Ala Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu Tyr
         50

<210> SEQ ID NO 9
<211> LENGTH: 54
<212> TYPE: PRT
<213> ORGANISM: Pentadiplandra brazzeana

<400> SEQUENCE: 9

Asp Lys Cys Lys Lys Val Tyr Glu Asn Tyr Pro Val Ser Lys Cys Gln
  1               5                  10                  15

Leu Arg Ala Asn Gln Cys Asn Tyr Asp Cys Lys Leu Asp Lys His Ala
             20                  25                  30

Arg Ser Gly Glu Cys Phe Tyr Asp Glu Lys Arg Asn Leu Gln Cys Ile
         35                  40                  45

Cys Asp Tyr Cys Glu Tyr
         50

<210> SEQ ID NO 10
<211> LENGTH: 53
<212> TYPE: PRT
<213> ORGANISM: Pentadiplandra brazzeana

<400> SEQUENCE: 10

Asp Lys Cys Lys Lys Val Tyr Glu Asn Tyr Pro Val Ser Lys Cys Ala
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu Tyr
         50

<210> SEQ ID NO 11
<211> LENGTH: 52
```

```
<212> TYPE: PRT
<213> ORGANISM: Pentadiplandra brazzeana

<400> SEQUENCE: 11

Asp Lys Cys Lys Lys Val Tyr Glu Asn Tyr Pro Val Ser Lys Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu
         50

<210> SEQ ID NO 12
<211> LENGTH: 53
<212> TYPE: PRT
<213> ORGANISM: Pentadiplandra brazzeana

<400> SEQUENCE: 12

Asn Lys Cys Lys Lys Val Tyr Glu Asn Tyr Pro Val Ser Lys Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu Tyr
         50

<210> SEQ ID NO 13
<211> LENGTH: 53
<212> TYPE: PRT
<213> ORGANISM: Pentadiplandra brazzeana

<400> SEQUENCE: 13

Asp Lys Cys Lys Lys Val Ala Glu Asn Tyr Pro Val Ser Lys Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Asp Tyr Cys Glu Tyr
         50

<210> SEQ ID NO 14
<211> LENGTH: 53
<212> TYPE: PRT
<213> ORGANISM: Pentadiplandra brazzeana

<400> SEQUENCE: 14

Asp Lys Cys Lys Lys Val Tyr Glu Asn Tyr Pro Val Ser Lys Cys Gln
  1               5                  10                  15

Leu Ala Asn Gln Cys Asn Tyr Asp Cys Lys Leu Asp Lys His Ala Arg
             20                  25                  30

Ser Gly Glu Cys Phe Tyr Asp Glu Lys Arg Asn Leu Gln Cys Ile Cys
         35                  40                  45

Ala Tyr Cys Glu Tyr
         50

<210> SEQ ID NO 15
```

```
<211> LENGTH: 162
<212> TYPE: DNA
<213> ORGANISM: Pentadiplandra brazzeana
<220> FEATURE:
<221> NAME/KEY: CDS
<222> LOCATION: (1)..(162)

<400> SEQUENCE: 15 gca gac aaa tgt aaa aaa gta tac gaa aac tac ccg gta tcc aaa tgt       48
Ala Asp Lys Cys Lys Lys Val Tyr Glu Asn Tyr Pro Val Ser Lys Cys
 1               5                  10                  15 cag ctg gca aac cag tgt aac tac gac tgt aaa ctg gac aaa cac gct       96
Gln Leu Ala Asn Gln Cys Asn Tyr Asp Cys Lys Leu Asp Lys His Ala
             20                  25                  30 cgt tcc ggt gaa tgc ttc tac gac gaa aaa cgt aac ctg cag tgc atc      144
Arg Ser Gly Glu Cys Phe Tyr Asp Glu Lys Arg Asn Leu Gln Cys Ile
         35                  40                  45 tgc gac tac tgc gaa tac                                              162
Cys Asp Tyr Cys Glu Tyr
         50

<210> SEQ ID NO 16
<211> LENGTH: 54
<212> TYPE: PRT
<213> ORGANISM: Pentadiplandra brazzeana

<400> SEQUENCE: 16

Ala Asp Lys Cys Lys Lys Val Tyr Glu Asn Tyr Pro Val Ser Lys Cys
 1               5                  10                  15

Gln Leu Ala Asn Gln Cys Asn Tyr Asp Cys Lys Leu Asp Lys His Ala
             20                  25                  30

Arg Ser Gly Glu Cys Phe Tyr Asp Glu Lys Arg Asn Leu Gln Cys Ile
         35                  40                  45

Cys Asp Tyr Cys Glu Tyr
         50

<210> SEQ ID NO 17
<211> LENGTH: 162
<212> TYPE: DNA
<213> ORGANISM: Pentadiplandra brazzeana
<220> FEATURE:
<221> NAME/KEY: CDS
<222> LOCATION: (1)..(162)

<400> SEQUENCE: 17 gac aaa tgt aaa aaa gta tac gaa aac tac ccg gta tcc aaa tgt cag       48
Asp Lys Cys Lys Lys Val Tyr Glu Asn Tyr Pro Val Ser Lys Cys Gln
 1               5                  10                  15 ctg cgt gca aac cag tgt aac tac gac tgt aaa ctg gac aaa cac gct       96
Leu Arg Ala Asn Gln Cys Asn Tyr Asp Cys Lys Leu Asp Lys His Ala
             20                  25                  30 cgt tcc ggt gaa tgc ttc tac gac gaa aaa cgt aac ctg cag tgc atc      144
Arg Ser Gly Glu Cys Phe Tyr Asp Glu Lys Arg Asn Leu Gln Cys Ile
         35                  40                  45 tgc gac tac tgc gaa tac                                              162
Cys Asp Tyr Cys Glu Tyr
         50

<210> SEQ ID NO 18
<211> LENGTH: 54
<212> TYPE: PRT
<213> ORGANISM: Pentadiplandra brazzeana

<400> SEQUENCE: 18
```

-continued

```
Asp Lys Cys Lys Lys Val Tyr Glu Asn Tyr Pro Val Ser Lys Cys Gln
 1               5                  10                  15

Leu Arg Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
 50
```